June 20, 1972 W. H. JESSEL, JR., ET AL Plant Pat. 3,214
CHRYSANTHEMUM PLANT
Filed Oct. 14, 1970
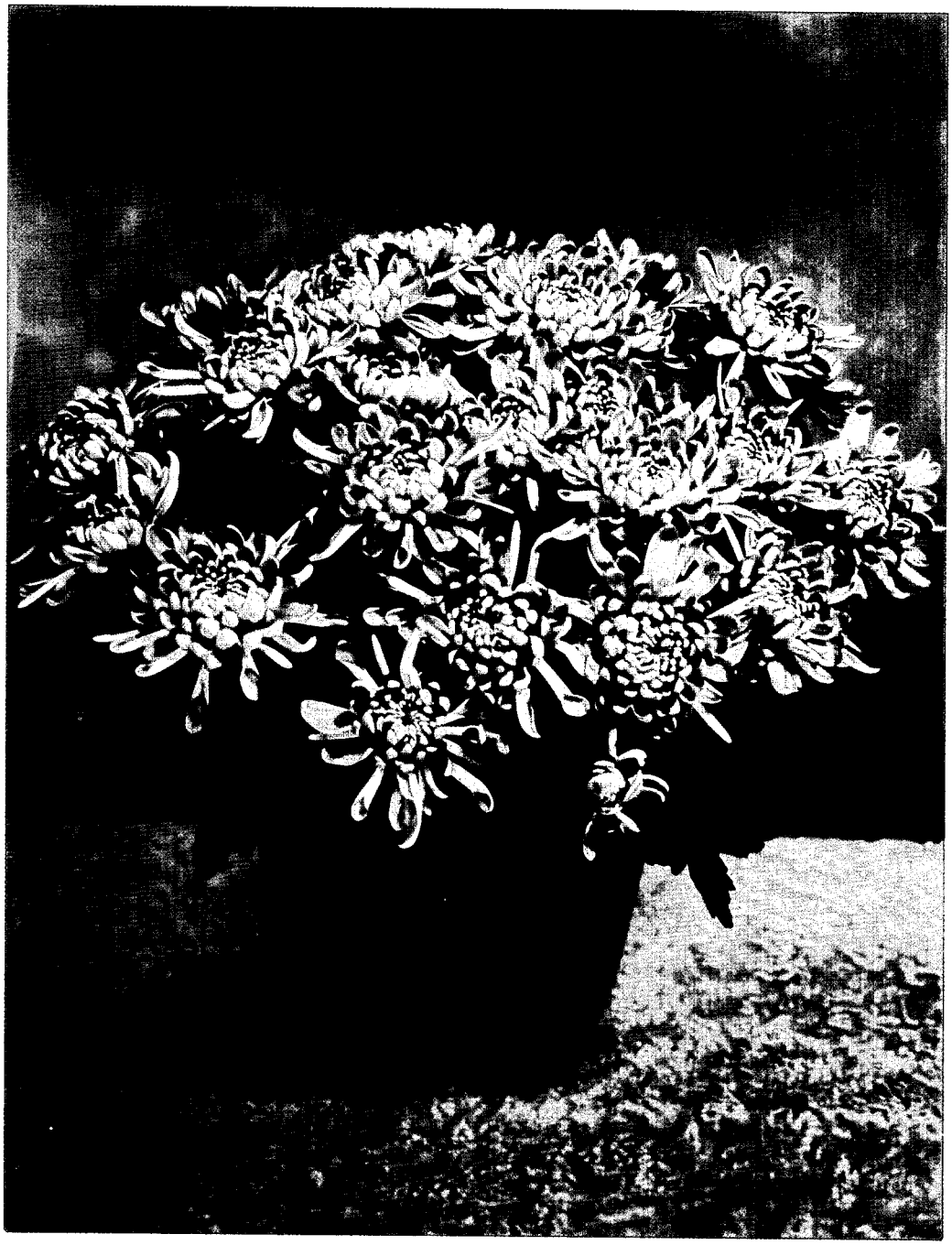
INVENTORS
WALTER H. JESSEL, JR.,
WILLIAM E. DUFFETT
BY
Oberlin, Maky, Donnelly & Renner
ATTORNEYS

United States Patent Office

Plant Pat. 3,214
Patented June 20, 1972

3,214
CHRYSANTHEMUM PLANT

Walter H. Jessel, Jr., Doylestown, and William E. Duffett, Akron, Ohio, assignors to Yoder Brothers, Inc., Barberton, Ohio

Filed Oct. 14, 1970, Ser. No. 80,822
Int. Cl. A01h *5/00*
U.S. Cl. Plt.—79 1 Claim

The present invention comprises a new and distinct cultivar of chrysanthemum plant which is a sport of the cultivar known in the United States as Orange Bowl, and unpatented but commercially well-known cultivar of Yoder Brothers, Inc., Barberton, Ohio, the assignee of the present invention.

The new cultivar is similar to the parent cultivar Orange Bowl in having the same characteristic of foliage shape. However, the new cultivar is distinguished from Orange Bowl by the following characteristics:

(1) Smaller flowers by approximately 1".
(2) More formal flowers—produces fewer spooned petals.
(3) Broader petals, more deeply keeled.
(4) A deeper color.
(5) Shorter, more compact habit.
(6) Smaller, darker foliage.
(7) Thirty percent more breaks.
(8) Three days earlier and more uniform response.
(9) Rudimentary stipules as contrasted with the small stipules of Orange Bowl.

(10) Longer period of value.—The cultivar is considered a year round cultivar as compared with the April through November recommendation for Orange Bowl in the north and northwest.

The new cultivar was selected from a flowering block of the parent cultivar in Barberton, Ohio, and when asexually reproduced by cuttings has been found to retain its distinctive characteristics through successive propagations.

The new cultivar when grown in the vicinity of Barberton, Ohio, has a response period of approximately 10 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States, including coastal California, is from January through December; in Florida, from November through June.

The accompanying drawing shows the unique characteristics of the new cultivar, the color being as nearly true as possible with color illustrations of this type.

In the description which follows, color references are to the Munsell Color Book, 1963 edition, and comparisons have been made with the cultivar Orange Bowl. It should be noted that some difficulty was encountered in color matching, and the color values indicated represent the closest available color keys.

BOTANICAL CLASSIFICATION

*Chrysanthemum morifolium*

| | Copper Bowl | Orange Bowl |
|---|---|---|
| Bloom: | | |
| Size | 3¾" | 5". |
| Fully expanded | 4¾" | 6". |
| Borne | Single on disbudded stems | Singly on disbudded stems. |
| Stems | Strong | Strong. |
| Form | Semi-incurve | Irregular incurve. |
| Permanence | 15–20 days | 15–20 days. |
| Color: | | |
| Center of flower | Greenish yellow, 10Y8.5/8 | Greenish yellow, 7.5Y8/10 to yellow 5Y8/10. |
| Base of petals | Red bronze, 1.25YR4/12 over yellow, 10YR8/14 | Bronze, 7.5YR5/8 over dark yellow, 2.5Y8.5/12. |
| Inside of petals | Red bronze, 1.25YR4/12 over yellow, 10YR8/14 to bronze, 10YR6/12 over dark yellow, 5Y8.5/12. | Bronze, 7.5YR5/8 over dark yellow, 2.5Y8.5/12 to light bronze, 2.5Y7/8 over dark yellow, 5Y8.5/12. |
| Reverse of petals | Light bronze, 5Y6/8 to light yellow bronze, 5Y7/8 | Yellow 5Y8/10 to light yellow, 5Y8/8. |
| Tonality from a distance | Red bronze to golden bronze | Orange bronze to golden yellow. |
| Discoloration | Light bronze | Golden bronze. |
| Petals: | | |
| Texture | Smooth | Smooth. |
| Appearance and form | Closed at base—broaden quickly, deeply keeled, tapering to a blunt hooded point. | Open at base—broaden quickly, shallow ridged keel, tapering to a blunt point. |
| Arrangement | Composite, whorled on a single receptacle | Composite, whorled on a single receptacle. |
| Persistence | Resist shatter | Resit shatter. |
| Fragrance | Typical chrysanthemum | Typical chrysanthemum. |
| Reproductive organs: | | |
| Stamen, anthers | None | None. |
| Pollen | do | Do. |
| Arrangement | Clustered in center of flower, if present | Clustered in center of flower, if present. |
| Styles | Present | Present. |
| Length | Short | Short. |
| Ovaries | At the base of petal attached to receptacle | At the base of petal attached to receptacle. |
| Plant: | | |
| Form | Herbaceous | Herbaceous. |
| Growth | Spreadiug | Spreading. |
| Height | Approximately 10–12" when given 10 week short treatment, as defined in the timetables of Yoder Brothers, Inc. | Approximately 12½–14½" when given 10 week short treatment as defined in the timetables of Yoder Brothers, Inc. |
| Spread | Approximately 8" as a single pinched plant when given 10 week short treatment as defined in the timetables of Yoder Brothers, Inc. | Approximately 10" as a single pinched plant when given 10 week short treatment as defined in the timetables of Yoder Brothers, Inc. |
| Foliage: | | |
| Top side | Dark green, 10GY2/4 | Dark green, 10GY3/4. |
| Size | 4" long, 2" wide | 4½" long, 2¾" wide. |
| Quantity | Numerous | Numerous. |
| Shape | Spatulate lobed | Spatulate lobed. |
| Texture | Smooth | Smooth. |
| Ribs and veins | Prominent | Prominent. |
| Edge | Moderately indented | Moderately indented. |
| Serration | Fine | Fine. |
| Underside | Light green, 7.5GY5/4 | Light green, 7.5GY5/4. |
| Stipules | Rudimentary | Small. |

We claim:

1. A new and distinct cultivar of chrysanthemum characterized particularly to the uniqueness as compared with the parent cultivar Orange Bowl by its smaller flowers by approximately 1", more formal flowers, with fewer spooned petals, broader petals, more deeply keeled, deeper color, shorter habit, smaller, darker foliage, 30 percent more breaks, 3 days earlier and more uniform response, rudimentary stipules, and a year round flowering period in the north and northwest.

No references cited.

ROBERT E. BAGWILL, Primary Examiner